(12) United States Patent
Hong et al.

(10) Patent No.: US 9,586,204 B2
(45) Date of Patent: Mar. 7, 2017

(54) PAPER SENSOR

(71) Applicant: Xerox Corporation, Norwalk, CT (US)

(72) Inventors: Wei Hong, Amherst, MA (US); Jing Zhou, Webster, NY (US); Mandakini Kanungo, Webster, NY (US); Xing Liu, Webster, NY (US); Nancy Y. Jia, Webster, NY (US); Sarah J. Vella, Milton, CA (US); Laura Lu, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 14/799,832

(22) Filed: Jul. 15, 2015

(65) Prior Publication Data

US 2016/0051980 A1     Feb. 25, 2016

Related U.S. Application Data

(60) Provisional application No. 62/041,174, filed on Aug. 25, 2014.

(51) Int. Cl.
*G01N 21/75* (2006.01)
*B01L 3/00* (2006.01)
*G01N 33/52* (2006.01)
*G01N 33/558* (2006.01)

(52) U.S. Cl.
CPC .......... *B01L 3/5023* (2013.01); *G01N 33/525* (2013.01); *G01N 33/558* (2013.01); *B01L 2300/069* (2013.01); *B01L 2300/0803* (2013.01); *B01L 2300/0864* (2013.01); *B01L 2300/0887* (2013.01); *B01L 2300/126* (2013.01); *B01L 2300/165* (2013.01)

(58) Field of Classification Search
CPC ................ B01L 3/5023; B01L 3/5025; B01L 2300/069; B01L 2300/165; B01L 2300/126; B01L 2300/0803; B01L 2300/0864; B01L 2300/0887; G01N 33/558; G01N 33/525
USPC ........................................................ 422/425
See application file for complete search history.

(56) References Cited

U.S. PATENT DOCUMENTS

| | | |
|---|---|---|
| 7,454,880 B1 | 11/2008 | Austin et al. |
| 7,969,624 B2 | 6/2011 | Mestha et al. |
| 8,249,879 B2 | 8/2012 | Bangalore et al. |
| 8,377,710 B2 | 2/2013 | Whitesides et al. |
| 8,628,729 B2 | 1/2014 | Carrilho et al. |
| 8,730,460 B2 | 5/2014 | Yan et al. |

(Continued)

*Primary Examiner* — Dennis M White
(74) *Attorney, Agent, or Firm* — Fay Sharpe LLP (57) ABSTRACT

The present disclosure proposes a design of a biomedical paper sensor which can determine the concentration of biological materials in fluids such as blood, urine, and saliva. The sensor contains a plurality of axially radiating test zones, each test zone separated from other test zones by wax ink barriers formed by a process that produces thin walls. Each test zone can contain a unique test reagent, or a unique concentration of a test reagent, and can also be identified by printed text. The region of the device outside of the test zone area is printed with a uniform reference color. Benefits of the invention include increased accuracy in the measurement of the concentration of biological materials due to the larger test zone area. Benefits also include the integration of the reference or calibration color which simplifies the calibration needed for quantification of the concentration.

17 Claims, 5 Drawing Sheets

(56) References Cited

U.S. PATENT DOCUMENTS

| | | |
|---|---|---|
| 8,821,810 B2 | 9/2014 | Whitesides et al. |
| 2007/0061393 A1 | 3/2007 | Moore |
| 2011/0111517 A1 | 5/2011 | Siegel et al. |
| 2011/0123398 A1 | 5/2011 | Carrilho et al. |
| 2012/0053930 A1 | 3/2012 | Bangalore et al. |
| 2012/0181184 A1 | 7/2012 | Whitesides et al. |
| 2012/0198685 A1 | 8/2012 | Bernardina Junior |
| 2012/0257188 A1 | 10/2012 | Yan et al. |
| 2013/0034869 A1 | 2/2013 | Whitesides et al. |
| 2013/0034908 A1* | 2/2013 | Barstis ............... G01N 31/22 436/43 |
| 2013/0084630 A1* | 4/2013 | Rolland ............... G01N 21/78 435/287.8 |

* cited by examiner

FIG. 7

PAPER SENSOR

This application claims priority to U.S. Provisional Patent Application No. 62/041,174, filed Aug. 25, 2014, by Wei Hong et al. and entitled "DESIGN OF PAPER SENSOR" and is incorporated herein by reference in its entirety.

CROSS REFERENCE TO RELATED PATENTS AND APPLICATIONS

U.S. Provisional Patent Application No. 62/041,191, filed Aug. 25, 2014, by Jia et al. and entitled "PAPER SENSING AND ANALYTIC SERVICE WORKFLOW METHODS AND SYSTEMS";

U.S. Provisional Patent Application No. 62/041,181, filed Aug. 25, 2014, by Zhou et al., and entitled "ROBUST COLORIMETRIC PROCESSING METHOD FOR PAPER BASED SENSORS";

U.S. patent application Ser. No. 14/312,061, filed Jun. 23, 2014, by Zhou et al., and entitled "APPARATUS FOR FORMING HYDROPHOBIC STRUCTURES IN POROUS SUBSTRATES";

U.S. patent application Ser. No. 14/312,209, filed Jun. 23, 2014, by Zhou et al., and entitled "APPARATUS FOR PRODUCING PAPER-BASED CHEMICAL ASSAY DEVICES";

U.S. patent application Ser. No. 14/311,970, filed Jun. 23, 2014, by Beachner et al., and entitled "SYSTEM AND METHOD FOR FORMING BONDED SUBSTRATES"; and U.S. patent application Ser. No. 14/311,909, filed Jun. 23, 2014, by O'Neil et al., and entitled "SYSTEM AND METHOD FOR FORMING HYDROPHOBIC STRUCTURES IN A POROUS SUBSTRATE", are incorporated herein by reference in their entirety.

BACKGROUND

Paper-based sensing (i.e. paper-based test devices) is an emerging technology that has advantages relative to traditional test strips in terms of cost and multiplexing. The concern of poor accuracy on paper-based sensors and paper test strips, due to the colorimetric measurement, has limited them from quantitative applications. In existing test strip applications, a user has to manually compare resultant colors to a set of colors on a separate reference card. This is neither user friendly nor reliable. Recently some companies have developed phone 'apps' to automate the test strip reading process using a phone camera.

INCORPORATION BY REFERENCE

U.S. Pat. No. 8,377,710, issued Feb. 19, 2013, by Whitesides et al., and entitled "LATERAL FLOW AND FLOW-THROUGH BIOASSAY DEVICES BASED ON PATTERNED POROUS MEDIA, METHODS OF MAKING SAME, AND METHODS OF USING SAME";

U.S. Patent Application Publication No. 2011/0111517, published May 12, 2011, by Siegel et al., and entitled "PAPER-BASED MICROFLUIDIC SYSTEMS";

U.S. Patent Application Publication No. 2011/0123398, published May 26, 2011, by Carrilho et al., and entitled "THREE-DIMENSIONAL MICROFLUIDIC DEVICES";

U.S. Patent Application Publication No. 2012/0053930, published Mar. 1, 2012, by Bangalore et al., and entitled "SYSTEM AND METHOD OF PROVIDING A SPOKEN DIALOG INTERFACE TO A WEBSITE";

U.S. Patent Application Publication No. 2012/0181184, published Jul. 19, 2011, by Whitesides et al., and entitled "MICROFLUIDIC, ELECTROCHEMICAL DEVICES";

U.S. Patent Application Publication No. 2012/0198685, published Aug. 9, 2012, by Bernardina Junior, and entitled "METHOD TO PRODUCE AN ELECTRODE WITH A LOW LEVEL OF HYDROGEN AND LOW ABSORPTION OF MOISTURE";

U.S. Patent Application Publication No. 2012/0257188, published Oct. 11, 2012, by Yan et al., and entitled "PAPER BASED SPECTROPHOTOMETRIC DETECTION OF BLOOD HEMOGLOBIN CONCENTRATION";

U.S. Patent Application Publication No. 2013/0034869, published Feb. 7, 2013, by Whitesides et al., and entitled "DEVICES AND METHODS FOR MULTIPLEXED ASSAYS"; and U.S. Patent Application Publication No. 2013/0084630, published Apr. 4, 2013, by Rolland et al., and entitled "QUANTITATIVE MICROFLUIDIC DEVICES", are incorporated herein by reference in their entirety.

BRIEF DESCRIPTION

The present disclosure provides for a biomedical paper sensor for determining a concentration of biological materials in fluids. The paper sensor comprises a plurality of axial symmetric test zone; wherein the test zones radiate outward from a central point. Each of the axial symmetric test zones can be divided by wax ink barrier walls. The axial symmetric test zones contain a unique test reagent therein. The paper sensor further comprises a reference region surrounding the plurality of axial test zones, wherein the reference region includes a calibration color area including a predeterminable color for comparing to one or more of the axial test zones.

The present disclosure further provides for a biomedical paper sensor for determining a concentration of biological materials and fluids. The paper sensor includes a plurality of axially radiating test zones, wherein each of the axially radiating test zones are divided by wax ink barrier walls. Each of the axially radiating test zones can contain a unique test reagent therein. The paper sensor further comprises a reference region surrounding the plurality of axially radiating test zones, wherein the reference region includes a calibration color area including a predeterminable color for comparing to one or more of the axially radiating test zones.

The present disclosure further provides for a biomedical paper sensor for determining a concentration of biological materials and fluids comprising a plurality of axially radiating test zones, wherein each of the axially radiating test zones can be divided by wax ink barrier walls. Each of the axially radiating test zones contain a unique test reagent therein. The paper sensor further comprises a reference region surrounding the plurality of axially radiating test zones. The device further comprises a total device area, including the combined areas of a reference region area and the axially radiating test zones area, wherein the axially radiating test zones area is at least 37.5% of the total device area and wherein the reference region area further includes a substrate region separating the axially radiating test zones area and the calibration color area.

The present disclosure additionally provides for a biomedical paper sensor for determining a concentration of biological materials and fluids comprising a bottom laminate film area; a plasma separation membrane layer; a structural forming layer; and, a top laminate film layer. The structural forming layer is adjacent to the top laminate film layer. The plasma separation membrane layer is between the bottom laminate film layer and the structural forming layer. The structural forming layer includes a plurality of axially radiating test zones, wherein each of the axially radiating test zones are divided by wax ink barrier walls.

DETAILED DESCRIPTION

Figure 1:
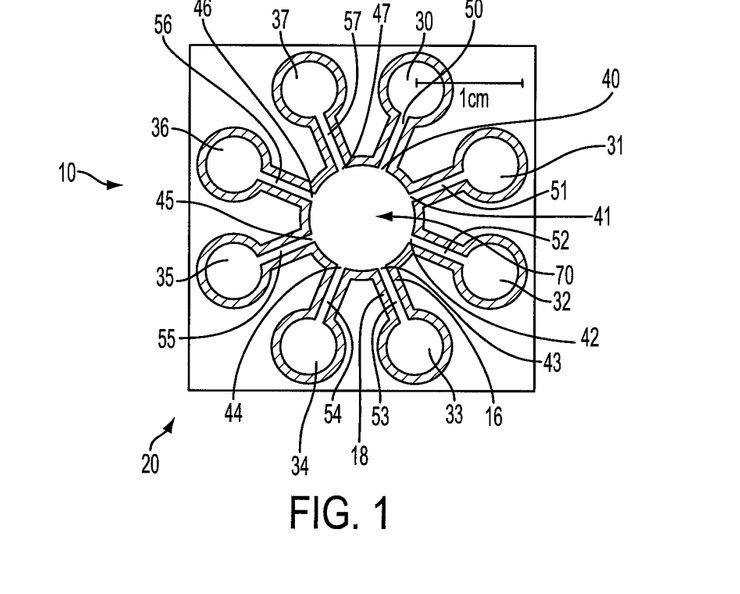
FIG. 1 represents one type of a paper based sensor or test device.
Figure 2:
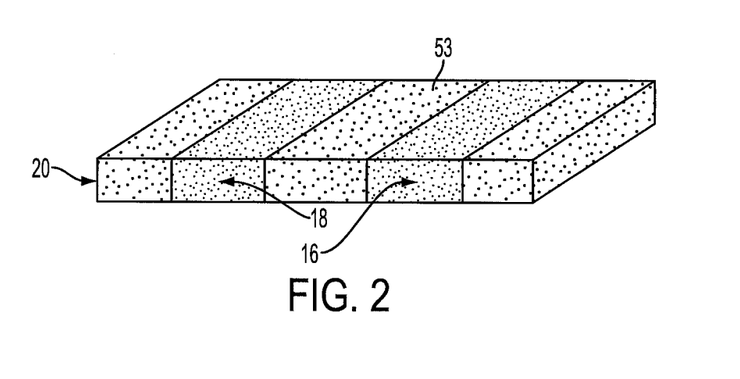
FIG. 2 represents an enlarged partial section of the paper-based sensor of FIG. 1.

A paper-based sensor or paper-based test device 10, as shown in FIGS. 1 and 2, is a small biomedical device made of paper, wax, and reagents that can analyze bioassays in test fluids or test liquids such as blood, urine and saliva. The hydrophobic barrier walls 16, 18 are made of wax that penetrates through the entire thickness of the paper 20 (i.e. hydrophilic matrix) to create and separate (i.e. divide) various fluidic components such as a series of test regions 30, 31, 32, 33, 34, 35, 36, 37, fluid entrances 40, 41, 42, 43, 44, 45, 46, 47, transport channels 50, 51, 52, 53, 54, 55, 56, 57, and mixers or reagents. The transport channels 50-57, can be hydrophobic (i.e. wax) channels extending through the hydrophilic matrix paper 20. Various reagents with various and/or different concentrations can be pre-deposited on the test regions 30-37. During the diagnostic process, capillary forces pull portions of the test fluid 70 to associated multiple test regions 30-37 and upon contacting the pre-deposited reagents, react with the respective portions of test fluid 70. A signal, color change, or color shade is generated if a specific analyte is present in the test fluid 70; for instance, a color shade or change develops where the color density varies as a result of the concentration of the analyte. The color change or shade can be captured and recorded by an imaging device such as a smart phone or camera phone and can then be processed by an algorithm to calculate the concentration of each analyte based on a calibration curve or color scale of the device. The diagnostic results and/or raw data (if the image processing and diagnostic analysis is done on the server side) can be uploaded to a data server where the user's or patient's history can be stored for inquiry and advanced data analytics can be performed which can help to detect and prevent adverse health conditions/diseases. It is to be appreciated that the user's data analytics or predictive analytics can be used for trend monitoring, health screening, risk assessment, et al.; the results of which can include non-adverse health conditions.

Paper based sensors have several advantages over traditional test strips. Test strips are simplex (one test per strip), while paper sensors can be multiplex (multiple tests on one device). Traditional test strips require relatively more test fluid than paper sensors. Test strips are fabricated by analog technology, while paper sensors can be digitally printed and quantitatively analyzed which enables greater customization and personalization.

Use of paper based sensors is an emerging technology that provides advantages over traditional test strips in terms of cost and multiplexing. The current paper based sensors require a user to provide a certain amount of test liquid (blood, urine, etc.) to ensure the accuracy of the test. The level of multiplexing is typically limited by the printing resolution and straightness of printed wax vertical walls/barriers. Additionally, the current method of reading colorimetric information uses either a separate manual reference card or uses a mobile application available in the market that can suffer from the variability for individual reading devices (camera, illumination, light conditions, surrounding light conditions, etc.). It is important to come up with novel designs for the paper based sensor that can achieve a higher level of multiplexing than the current devices available in the market, and can provide higher readout accuracy regardless of the variation from individual reading devices.

The present disclosure (referring to FIGS. 3-7) provides for a design and construction of paper sensors or test devices 100 that have an increased total test area relative to an overall fixed device area. This novel design and construction increases the extent of multiplexing and improves the readout accuracy. The present disclosure provides for a device 100 that includes several unique features. The resolution of the wax barriers are high so that the device can achieve higher levels of multiplexing and can include larger overall test area, relative to the overall device area, for increased read out accuracy. A reference region, including a calibration color area, can be directly printed on the paper sensor for direct side-by-side comparison to the corresponding colorimetric reactions in respective test regions. This can eliminate the use of a separate reference card, which has been heretofore necessary for 'reading' and interpreting paper-based sensors.

Prior art paper based sensors 10 (FIGS. 1-2) are typically made through a manual oven process. The wax in hydrophobic channels 50-57 needs to spread more laterally (reflow) to achieve a total penetration through the paper. As a result, the size of the test areas 30-37 and the level of multiplexing are limited relative to an overall fixed device size due to the non-uniformity/large channel variation caused by uncontrolled reflow of wax. In contrast, the device fabricated using the controlled process described in U.S. patent application Ser. No. 14/311,909, filed Jun. 23, 2014, by O'Neil et al., and entitled "SYSTEM AND METHOD FOR FORMING HYDROPHOBIC STRUCTURES IN A POROUS SUBSTRATE" (incorporated herein by reference), has a higher resolution and outstanding channel uniformity. These advantages enable the paper based sensor to achieve the design and construction as described hereinafter.

Figure 3:
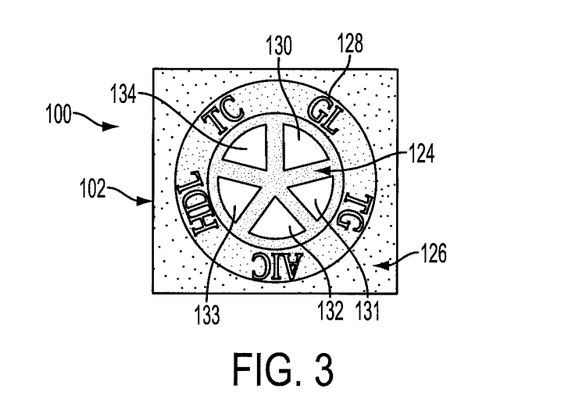
FIG. 3 shows a top elevational view of an exemplary paper-based test device including a reference calibration color area, a plurality of test zones, a plurality of ink barriers, and a label area.
Figure 4:
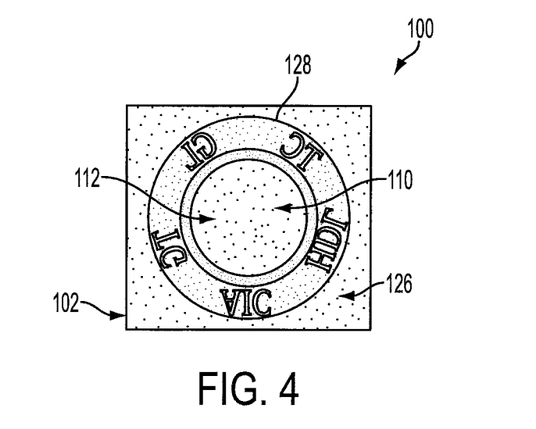
FIG. 4 shows a bottom elevational view of an exemplary paper-based test device shown in FIG. 3.

Referring now to FIGS. 3 and 4, some of the features of the paper-based sensor 100 disclosed herein include: larger test area 110, including segmented test zones 130, 131, 132, 133, 134, relative to an overall fixed size device area 102 compared to prior art sensors; and, fully utilized plasma separation membrane layer 112 on the backside of the device for improved separation of plasma from the blood. The paper-based sensor 100 can include a channel structural area 124 which increases the readout accuracy and level of multiplexing without requiring a larger test sample (i.e. blood). A reference or calibration reference color area 126 can include a distinct area and can be directly printed on the device either as part of the channel structure or as an additional pattern. An auxiliary information area 128 can surround the test area 110.

In another exemplary embodiment (FIG. 5), a paper sensor device 200 can include the following components: a structural forming layer 216, an optional filter membrane layer 212, and at least two laminating layers 218, 220. The structure forming layer 216 can include a channel structural area 224, a test area 210, a calibration reference area 226, and auxiliary information area 228.

Figure 5:
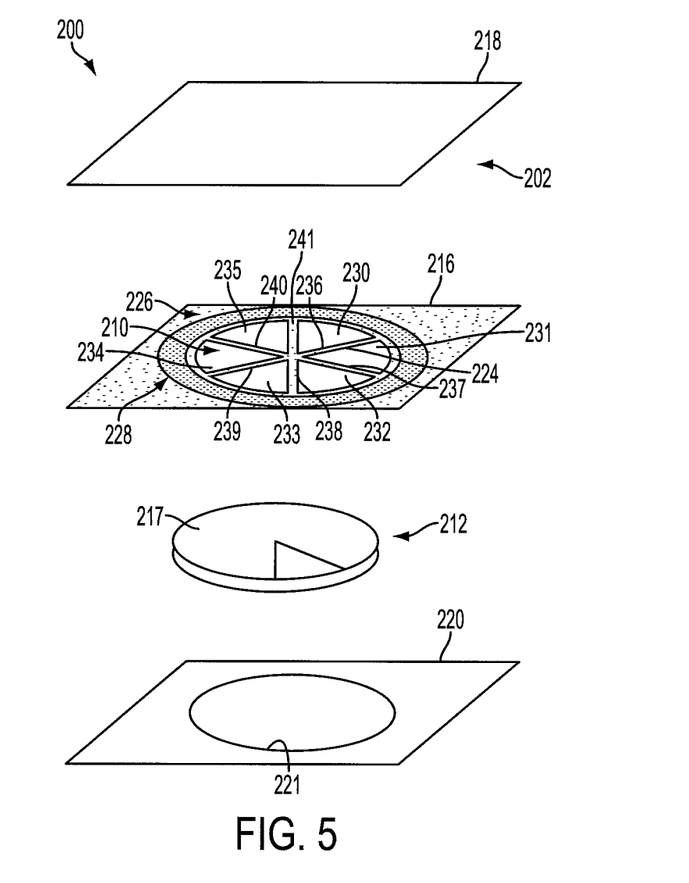
FIG. 5 is an exploded view of a paper based sensor according to the present disclosure.

The test zone or test area 210 can include 1 to n (n>=2) individual segmented test zones 230, 231, 232, 233, 234, 235. The segmented test zones 230-235 can be arranged in an axially symmetric or axially radiating manner. The total test area 210 is from about 25% to about 60%, and preferably at least 37.5% of the total device area 202. The minimum area of individual test zones 230-235 can be about 5 mm$^2$. Comparing to the prior art devices (FIG. 1), the individual test zones 230-235, of the present disclosure, are at least three (3) times larger. Test zones 230-235 are surrounded and divided by wax ink barrier walls 236, 237, 238, 239, 240, 241 (i.e. solid ink barriers) with a wall width of about 100 um for maximizing the area of the test regions or zones 230-235 relative to a limited space or area for the device 202. It is to be appreciated that a majority of the volume of a test sample is utilized and reaches, i.e. reacts with, the reagents in each of the test zones 230-235.

One exemplary test panel can include respective reagents in test zones 230-235 for measuring levels of triglyceride, total cholesterol, HDL (i.e. three individual test zones). Another exemplary test panel can include respective reagents in test zones for measuring lipid panel, i.e. levels of triglyceride, total cholesterol, HDL, Hemoglobin A1C (HbA1C), glucose (i.e. five individual test zones). In the aforementioned manner, each test zone 230-235 has a different reagent. It is to be appreciated that each test zone can alternatively have a different concentration of the same reagent to measure different levels of a single bioassay.

Auxiliary information or Identifying text (for example, GL, TG, HbA1C, HDL, TC labels; manufacturer name and date; etc.) that indicates the type of test in each test zone 230-235 can be printed outside and adjacent to the test zones or regions (i.e. auxiliary information area 228). Auxiliary information or identifying text (for example, GL represents glucose, TG represents triglyceride, A1C represents hemoglobin, HDL represents HDL cholesterol, and TC represents total cholesterol) labels the type of test in each test zone 230-235 and can be printed outside and adjacent to the test zones or regions (i.e. reference regions).

The optional filter membrane layer 212 can have a separation membrane 217 (i.e. plasma separation) that covers the total test area 210. Alternatively the optional filter membrane 217 can have a partial separation membrane and partial "other materials" (i.e. paper) to enable the controlled flow of the test sample. The plasma separation membrane 217 can include a series of pores on the top surface as well as the bottom surface. The series of pores can have a pore sized gradient between the top surface and the bottom surface. In particular, the pore size on the top surface can be greater than the pore size on the bottom surface.

Membrane layer 212 and structural forming layer 216 can be sandwiched between laminate film layers 218, 220. A hole 221 that is smaller than the size of the membrane 217 can be cut in the bottom lamination layer 220 at the backside of the device (FIG. 5). The plasma separation membrane 217 is visible on the backside of the device 200 when the device 200 is in the assembled arrangement.

Referring again to FIG. 5, the present disclosure proposes a design of a biomedical paper sensor 200 which can determine the concentration of biological materials in fluids such as blood, urine, and saliva. The sensor 200 can contain axially radiating and/or axially symmetric test zones 230-235 arranged similar to slices of a pie (for example) divided by wax ink barriers 236-241 formed by a process that produces thin walls. Each test zone 230-235 can contain a unique test reagent and is identified by printed text (not shown) in area 228. The region 226 of the device outside of the test zone 230-235 can be printed with a uniform reference color. Additionally, the color of the wax wall can also serve as a reference color when it is not clear. Benefits of the sensor 200 include increased accuracy in the measurement of the concentration of biological materials due to the larger area of the test zones. Benefits also include the integration of the reference or calibration color 226 into the sensor 200 which simplifies a visual calibration review, check, or comparison for quantification of the concentration of the test fluid (i.e. test sample).

Figure 6:
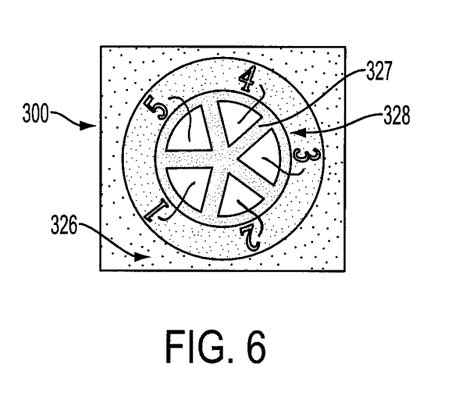
FIG. 6 is an exemplary Triglyceride test paper sensor.

Referring now to FIG. 6, wherein an exemplary Triglyceride paper sensor 300 is therein displayed. Identifying a reference or calibration color area can include a substrate region or auxiliary information area 328 between the test zones 1, 2, 3, 4, 5 and calibration color areas or regions 326, 327. Areas 326, 327, and 328 can be used as reference color areas or contrast color areas. Areas 327 and 328 can be any color to provide contrast (black, color, contrast color, etc.) between the test zones 1-5 and reference areas 326, 327, and 328. It is to be appreciated that the calibration reference area 326 can be separated into multiple sub-areas including separate reference colors associated with each sub-area (not shown). The multiple color reference areas enable use of reagents with different dye colors in test zones 1-5. Alternatively, the reference region can include a first calibration color area including a first predeterminable color for comparing to one or more of the axial test zones. The reference region can further include a second calibration color area including a second predeterminable color for comparing to one or more of the axial test zones. The first and second calibration color areas can each include first and second predeterminable colors, respectively, for comparing to one or more of the axial test zones to report or indicate the concentration of at least two test substance analytes based on the calibrated reading in each test area. In one embodiment, the substrate region 328 can include a contrasting color to distinguish between the test zones 1-5 and the calibration color area 326. Although not shown in FIG. 6, the Triglyceride paper sensor 300 can display a gradient of color change in the test zones 1-5 due to different concentrations of the Triglyceride. The color change or color shade of test zones 1-5 can be compared to the reference color 326 (i.e. magenta). It is to be appreciated that the color change or color density represents the concentration of Triglyceride (for example) from associated test zones 1, 2, 3, 4, 5 and can include concentrations of 100, 150, 200, 250, 300 mg/dL, respectively.

Figure 7:
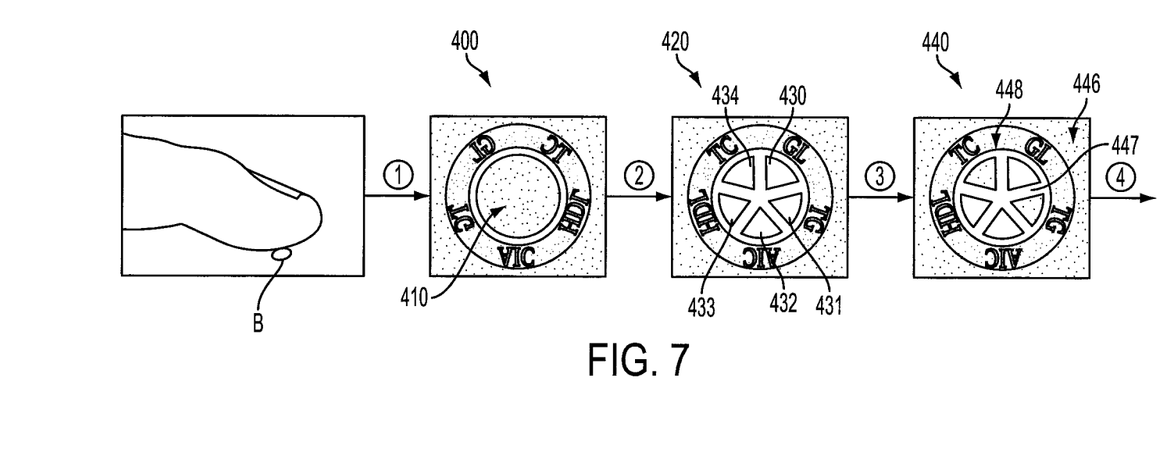
FIG. 7 is a representative display of the paper sensor device and a depiction of a method for using.

FIG. 7 displays a method of using a paper sensor device 400. A blood sample B is taken from a patient or user and placed or 'sucked' into the bottom, i.e. the test area 410, of the paper sensor 400 (step 1). The paper sensor 400 can be turned right side up wherein the blood sample processing can be viewed 420 (step 2). The assay development proceeds in which the blood sample B makes contact with the respective reagents in the test zones 430, 431, 432, 433, 434 (step 3). After the sample has reacted to the reagents, the developed assay is subsequently formed 440 (step 4). Identifying a reference or calibration color area can include substrate regions 447 and 448 between the test zones 430-434 and a calibration color area or region 446. The substrate regions 447 and 448 can include contrasting colors to distinguish between the test zones 430-434 and the calibration color area 446. In the example shown in FIG. 7, the paper sensor 400 can display a gradient of color change in the test zones 430-434 due to different types of reagents, and/or different concentrations of a reagent, that can measure different levels of a bioassay. It is to be appreciated that each type of analyte (GL, TG, HbAlC, HDL, TC) can use a different reagent, and each analyte/reagent pair can have an associated calibration curve for color reference. Additionally, for a single analyte assay determination, color change in the test zones 430-434 can be due to different concentrations of the same reagent in each test zone. The test zones 430-434 can be compared to the calibration or reference color 446 (i.e. magenta). In this manner, the biomedical paper sensor 400 is used for determining a concentration of biological materials contained in fluids (i.e. blood sample).

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiment also relates to an apparatus for performing the operations discussed herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

A machine-readable medium includes any mechanism for storing or transmitting information in a form readable by a machine (e.g., a computer). For instance, a machine-readable medium includes read only memory ("ROM"); random access memory ("RAM"); magnetic disk storage media; optical storage media; flash memory devices; and electrical, optical, acoustical or other form of propagated signals (e.g., carrier waves, infrared signals, digital signals, etc.), just to mention a few examples.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use.

Alternatively, the method may be implemented in transitory media, such as a transmittable carrier wave in which the control program is embodied as a data signal using transmission media, such as acoustic or light waves, such as those generated during radio wave and infrared data communications, and the like.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A biomedical paper sensor for determining a concentration of biological materials in fluids comprising:
   a plurality of axial symmetric test zones;
   wherein the test zones radiate outward from a central point;
   each of the axial symmetric test zones divided by wax ink barrier walls;
   each of the axial symmetric test zones contain a unique test reagent therein;
   a reference region surrounding the plurality of axial test zones; and,
   wherein the reference region includes a plurality of calibration color sub-areas including a distinct predeterminable color for each sub-area to compare to each one of the associated plurality of the axial test zones.

2. The paper sensor of claim 1, wherein the plurality of test zones is at least two.

3. The paper sensor of claim 1, further comprising:
a total device area including the combined areas of a reference region area and the axial test zones area; and,
wherein the axial test zones area is at least 37.5% of the total device area.

4. The paper sensor of claim 3, wherein the reference region area further includes a substrate region separating the axial test zones area and the calibration color area.

5. The paper sensor of claim 1, wherein an area of each of the axial symmetric test zones is at least 5 mm$^2$.

6. The paper sensor of claim 1, wherein the wax ink barrier walls include a thickness of about 100 μm.

7. The paper sensor of claim 1, further comprising:
a plasma separation membrane layer.

8. The paper sensor of claim 7, wherein said plasma separation layer includes a series of pores on a top surface and a bottom surface; and,
said series of pores have a pore size gradient between said top surface and said bottom surface.

9. The paper sensor of claim 8, wherein said pore size on said top surface is greater than said pore size on said bottom surface.

10. A biomedical paper sensor for determining a concentration of biological materials in fluids comprising:
a plurality of axially radiating test zones;
each of the axially radiating test zones divided by wax ink barrier walls;
each of the axially radiating test zones contain a unique concentration of a test reagent therein;
a reference region surrounding the plurality of axially radiating test zones;
wherein the reference region includes a calibration color area including a predeterminable color for comparing to each one of the plurality of axially radiating test zones; and,
wherein each one of the plurality of axially radiating test zones display a gradient of color change due to the unique concentration of a test reagent therein for a single analyte assay determination.

11. The paper sensor of claim 10, further comprising:
a total device area including the combined areas of a reference region area and the axially radiating test zones area; and,
wherein the axially radiating test zones area is at least 37.5% of the total device area.

12. The paper sensor of claim 11, wherein the reference region area further includes a substrate region separating the axially radiating test zones area and the calibration color area.

13. The paper sensor of claim 10, wherein an area of each of the axially radiating test zones is at least 5 mm$^2$.

14. The paper sensor of claim 10, wherein the wax ink barrier walls include a thickness of about 100 μm.

15. A biomedical paper sensor for determining a concentration of biological materials in fluids comprising:
a plurality of axially radiating test zones;
each of the axially radiating test zones divided by wax ink barrier walls;
each of the axially radiating test zones contain a unique test reagent therein;
a reference region surrounding the plurality of axially radiating test zones;
a total device area including the combined areas of a reference region area and the axially radiating test zones area;
wherein the axially radiating test zones area is at least 37.5% of the total device area;
wherein the reference region area further includes a substrate region separating the axially radiating test zones area and a calibration color area; and,
the calibration color area including a predeterminable color for comparing to each one of the plurality of axially radiating test zones.

16. The paper sensor of claim 15, wherein an area of each of the axially radiating test zones is at least 5 mm$^2$.

17. The paper sensor of claim 15, wherein the wax ink barrier walls include a thickness of about 100 μm.

\* \* \* \* \*